United States Patent
Kyal et al.

(10) Patent No.: US 9,320,440 B2
(45) Date of Patent: Apr. 26, 2016

(54) DISCRIMINATING BETWEEN ATRIAL FIBRILLATION AND SINUS RHYTHM IN PHYSIOLOGICAL SIGNALS OBTAINED FROM VIDEO

(71) Applicant: Xerox Corporation, Norwalk, CT (US)

(72) Inventors: Survi Kyal, Rochester, NY (US); Lalit Keshav Mestha, Fairport, NY (US); Jean-Philippe Couderc, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 102 days.

(21) Appl. No.: 14/242,322

(22) Filed: Apr. 1, 2014

(65) Prior Publication Data
US 2015/0272456 A1    Oct. 1, 2015

(51) Int. Cl.
A61B 5/02     (2006.01)
A61B 5/00     (2006.01)
A61B 5/0295   (2006.01)
A61B 5/107    (2006.01)

(52) U.S. Cl.
CPC ............. *A61B 5/0077* (2013.01); *A61B 5/0082* (2013.01); *A61B 5/0295* (2013.01); *A61B 5/1073* (2013.01)

(58) Field of Classification Search
CPC . A61B 5/0044; A61B 5/02416; A61B 5/0452
See application file for complete search history.

(56) References Cited

U.S. PATENT DOCUMENTS

| | | | |
|---|---|---|---|
| 8,520,074 B2 | 8/2013 | Wang et al. | |
| 8,587,657 B2 | 11/2013 | Wang et al. | |
| 8,600,213 B2 | 12/2013 | Mestha et al. | |
| 8,617,081 B2 | 12/2013 | Mestha et al. | |
| 2009/0265671 A1* | 10/2009 | Sachs | G06F 3/017 715/863 |
| 2012/0263357 A1 | 10/2012 | Xu et al. | |
| 2012/0314759 A1* | 12/2012 | Huang | H04N 21/2343 375/240.02 |
| 2013/0077823 A1 | 3/2013 | Mestha et al. | |
| 2013/0147959 A1 | 6/2013 | Wang et al. | |
| 2013/0197380 A1* | 8/2013 | Oral | A61B 5/0452 600/518 |
| 2013/0215244 A1 | 8/2013 | Mestha et al. | |
| 2013/0218028 A1 | 8/2013 | Mestha et al. | |

(Continued)

OTHER PUBLICATIONS

Mestha et al., "Method and Apparatus for Monitoring a Subject for Atrial Fibrillation", U.S. Appl. No. 13/937,740, filed Jul. 9, 2013.

(Continued)

*Primary Examiner* — Mark Remaly
(74) *Attorney, Agent, or Firm* — Philip E. Blair; Fleit Gibbons Gutman Bongini & Bianco P.L.

(57) ABSTRACT

What is disclosed is a system and method for determining whether a subject is in atrial fibrillation. A video is received of a region of exposed skin of a subject. The video is acquired of a region where a videoplethysmographic (VPG) signal can be registered by at least one imaging channel of a video imaging device. For each batch of image frames, pixels associated with the region of exposed skin are isolated and processed to obtain a time-series signal. A VPG signal is extracted from the time-series signal. The power spectral density (PSD) is computed across all frequencies within the VPG signal. A pulse harmonic strength (PHS) is calculated for this VPG signal. The pulse harmonic strength is compared to a discrimination threshold, defined herein. A determination is made whether the subject in the video is in atrial fibrillation or in normal sinus rhythm.

28 Claims, 15 Drawing Sheets

(56) References Cited

U.S. PATENT DOCUMENTS

2013/0322729 A1   12/2013   Mestha et al.
2013/0345568 A1   12/2013   Mestha et al.
2013/0345569 A1   12/2013   Mestha et al.

OTHER PUBLICATIONS

Mestha et al., "System and Method for Determining Video-Based Pulse Transit Time With Time-Series Signals", U.S. Appl. No. 14/026,739, filed Jan. 9, 2014.

Kyal et al., "Continuous Cardiac Signal Generation From a Video of a Subject Being Monitored for Cardiac Function", U.S. Appl. No. 13/871,766, filed Apr. 26, 2013.

Kyal et al., "Continuous Cardiac Pulse Rate Estimation From Multi-Channel Source Video Data With Mid-Point Stitching", U.S. Appl. No. 13/871,728, filed Apr. 26, 2013.

Tanaka et al., "Processing Source Video for Real-Time Enhancement of a Signal of Interest", U.S. Appl. No. 13/745,283, filed Jan. 18, 2013.

Kyal et al., "A Method to Detect Cardiac Arrhythmias with a Webcam", Signal Processing in Medicine and Biology Symposium (SPMB), 2013 IEEE.

\* cited by examiner

|  | SR | AF | Δ=AF-SR | p-VALUE |
|---|---|---|---|---|
| VIDEOPLETHYMOGRAPHY | | | | |
| PR (ppm) | 57 (7) | 72 (9) | 15 (1) | <0.0001 |
| PHS (n.u.) | 5.1 (3.0) | 0.8 (0.2) | -4.9 (0.5) | <0.0001 |
| SDRR (ms) | 111 (27) | 175 (60) | 57 (9) | <0.0001 |
| RMSSD (ms) | 139 (33) | 232 (98) | 83 (12) | <0.0001 |
| pNN50 (%) | 50 (10) | 65 (4) | 16 (2) | <0.0001 |
| SD1 (ms) | 102 (26) | 168 (91) | 58 (10) | <0.0001 |
| SD2 (ms) | 106 (42) | 168 (91) | 37 (8) | <0.001 |
| ELECTROCARDIOGRAPHY | | | | |
| HR (bpm) | 56 (7) | 80 (17) | 23 (1) | <0.0001 |
| SDRR (ms) | 55 (29) | 166 (34) | 112 (6) | <0.0001 |
| RMSSD (ms) | 69 (40) | 234 (46) | 168 (9) | <0.0001 |
| pNN50 (%) | 15 (13) | 73 (5) | 58 (2) | <0.0001 |
| SD1 (ms) | 51 (30) | 171 (34) | 122 (7) | <0.0001 |
| SD2 (ms) | 100 (22) | 137 (22) | 37 (8) | <0.0001 |

FIG. 15

DISCRIMINATING BETWEEN ATRIAL FIBRILLATION AND SINUS RHYTHM IN PHYSIOLOGICAL SIGNALS OBTAINED FROM VIDEO

TECHNICAL FIELD

The present invention is directed to systems and methods for processing video of a subject such that a determination can be made whether that subject is in atrial fibrillation or in normal sinus rhythm.

BACKGROUND

Monitoring cardiac events is of clinical importance in the early detection of potentially fatal conditions. Current technologies involve contact sensors (e.g., ECG) the individual must wear constantly. Such a requirement can lead to patient discomfort, dependency, loss of dignity, and further may fail due to a variety of reasons including refusal to wear the monitoring device. Elderly cardiac patients are even more likely to suffer from the adverse effects of continued monitoring. The ability to monitor cardiac function by non-contact means is highly desirable in the healthcare industry. Measurements can be made without disturbing the resting patient, and will be suitable for long observation/monitoring periods and can provide a record of visual imagery of such patients. Video-based methods offer abilities to detect pulsation for long term cardiac function monitoring in a non-contact, unobtrusive manner.

Among cardiac arrhythmias, atrial fibrillation (AF) represents ⅓ of hospital admissions for cardiac-related issues. AF is one of the most common arrhythmias and can cause palpitations, fainting, chest pain, heart failure, and stroke. AF tends to increase with age and often presents with a wide spectrum of symptoms. Presently, there are over 2 million Americans diagnosed with AF. Unobtrusive, non-contact, imaging based methods are needed for monitoring patients for AF such that diagnosis and treatment can be improved. Much work has been done in this regard. The present invention is directed towards this issue.

Accordingly, what is needed in this art are increasingly sophisticated systems and methods for processing video of a subject such that a determination can be made whether that subject is in atrial fibrillation.

INCORPORATED REFERENCES

The following U.S. Patents, U.S. Patent Applications, and Publications are incorporated herein in their entirety by reference.

"Determining Cardiac Arrhythmia From A Video Of A Subject Being Monitored For Cardiac Function", U.S. Pat. No. 8,768,438, by Mestha et al.

"Continuous Cardiac Signal Generation From A Video Of A Subject Being Monitored For Cardiac Function", U.S. patent application Ser. No. 13/871,766, by Kyal et al.

"Continuous Cardiac Pulse Rate Estimation From Multi-Channel Source Video Data With Mid-Point Stitching", U.S. Pat. No. 9,036,877, by Kyal et al.

"Estimating Cardiac Pulse Recovery From Multi-Channel Source Data Via Constrained Source Separation", U.S. Pat. No. 8,617,081, by Mestha et al.

"Filtering Source Video Data Via Independent Component Selection", U.S. Pat. No. 8,600,213, by Mestha et al.

"Determining A Total Number Of People In An IR Image Obtained Via An IR Imaging System", U.S. Pat. No. 8,520,074, by Wang et al.

"Determining A Number Of Objects In An IR Image", U.S. Pat. No. 8,587,657, by Wang et al.

"Determining A Pixel Classification Threshold For Vehicle Occupancy Detection", U.S. Pat. No. 9,202,118, by Wang et al.

"Deriving Arterial Pulse Transit Time From A Source Video Image", U.S. Pat. No. 8,838,209, by Mestha.

"Video-Based Estimation Of Heart Rate Variability", U.S. Pat. No. 8,977,347, by Mestha et al.

"Systems And Methods For Non-Contact Heart Rate Sensing", U.S. Pat. No. 9,020,185, by Mestha et al.

"Processing A Video For Vascular Pattern Detection And Cardiac Function Analysis", U.S. Pat. No. 8,897,522, by Mestha et al.

"Subcutaneous Vein Pattern Detection Via Multi-Spectral IR Imaging In An Identity Verification System", U.S. Pat. No. 8,509,495, by Xu et al.

"Method And Apparatus For Monitoring A Subject For Atrial Fibrillation", U.S. patent application Ser. No. 13/937,740, by Mestha et al.

"System And Method For Determining Video-Based Pulse Transit Time With Time-Series Signals", U.S. patent application Ser. No. 14/026,739, by Mestha et al.

"Processing Source Video For Real-Time Enhancement Of A Signal Of Interest", U.S. Pat. No. 8,879,867, by Tanaka et al.

"Removing Environment Factors From Signals Generated From Video Images Captured For Biomedical Measurements", U.S. Pat. No. 9,185,353, by Mestha et al.

BRIEF SUMMARY

What is disclosed is a system and method for processing video of a subject such that a determination can be made whether that subject is in atrial fibrillation. The teachings hereof are directed to detecting AF episodes by analyzing videoplethysmographic (VPG) signals extracted from time-series signals generated from video. With an implementation of the teachings hereof, cardiac arrhythmias can be discovered in real-time or processed offline from a video of the resting cardiac patient. The system and methods disclosed herein provide an effective tool for AF detection and cardiac function assessment.

One embodiment of the present method for determining whether a subject is having an atrial fibrillation event involves performing the following. First, a video of a region of exposed skin of a subject is received. The video is acquired of a region where a videoplethysmographic (VPG) signal can be registered by at least one imaging channel of a video imaging device used to capture that video. A size N of a batch of image frames is defined. Batch of image frames of size N the following are performed. The batch of image frames is processed to isolate pixels associated with the region of exposed skin and the isolated pixels are processed to obtain a time-series signal for this batch. A VPG signal is extracted from this time-series signal. Thereafter, a power spectral density is computed across all frequencies within the VPG signal to facilitate an identification of a fundamental frequency and at least a first harmonic of the fundamental frequency. A pulse harmonic strength (PHS) is calculated comprising a ratio of signal strength at the identified fundamental frequency and harmonics to a strength of a base signal without these fundamental frequencies and harmonics. A pre-defined discrimination threshold can be selected using a Receiver Operating Characteristic (ROC) curve which is constructed for various values of the pulse harmonic strength. Using this selection of discrimination threshold a comparison is made to the calculated pulse harmonic strength from the VPG signal. As a result of the comparison, a determination is made whether the subject is in atrial fibrillation or in normal sinus rhythm. A pre-defined discrimination threshold can also be selected on an individual patient basis based on VPG signals obtained during atrial fibrillation and during sinus rhythm.

Many features and advantages of the above-described system and method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which:

FIG. 15 is a table showing average values and standard errors for the parameters measuring the dispersion of the heart and the pulsatile rates;

DETAILED DESCRIPTION

What is disclosed is a system and method for processing video of a subject such that a determination can be made whether that subject is in atrial fibrillation.

NON-LIMITING DEFINITIONS

"Atrial fibrillation" (AF or A-fib), is one of the most common cardiac arrhythmias. In AF, the normal regular electrical impulses generated by the sinoatrial node are overwhelmed by disorganized electrical impulses usually originating in the roots of the pulmonary veins, leading to irregular conduction of impulses to the ventricles which generate the heartbeat. AF increases the risk of stroke. The degree of stroke risk can be up to seven times that of the average population depending on the presence of additional risk factors such as high blood pressure. Around 15% of ischemic strokes are directly attributed to emboli in the setting of AF. Nearly 25% of additional ischemic strokes in which no cause can be identified may also be due to asymptomatic AF. A substantial percentage of patients with AF have no symptoms during brief periods or even sustained episodes of AF, making detection of AF in patients at high risk for stroke challenging with current technology over long term follow-up. AF may occur in episodes lasting from minutes to days, or be permanent in nature. A number of medical conditions increase the risk of AF. Atrial fibrillation may be treated with medications which either slow the heart rate to a normal range or revert the heart rhythm back to normal. The teachings hereof help identify asymptomatic AF patients at an early stage. The identification of subclinical AF is extremely important because early detection directly affects management as the majority of these patients can be effectively treated with systemic anticoagulation once AF has been determined.

A "subject" refers to a living being monitored for atrial fibrillation in accordance with the methods disclosed herein. Although the term "person" or "patient" may be used throughout this disclosure, it should be appreciated that the subject may be something other than a person such as, for example, a primate. Therefore, the use of such terms is not to be viewed as limiting the scope of the appended claims strictly to humans.

A "video" refers to a plurality of time-sequential image frames captured by a video imaging device, as is generally understood. The video may also contain other components such as, audio, time, frame rate data, and the like. The video is captured by a video imaging device.

Figure 1:
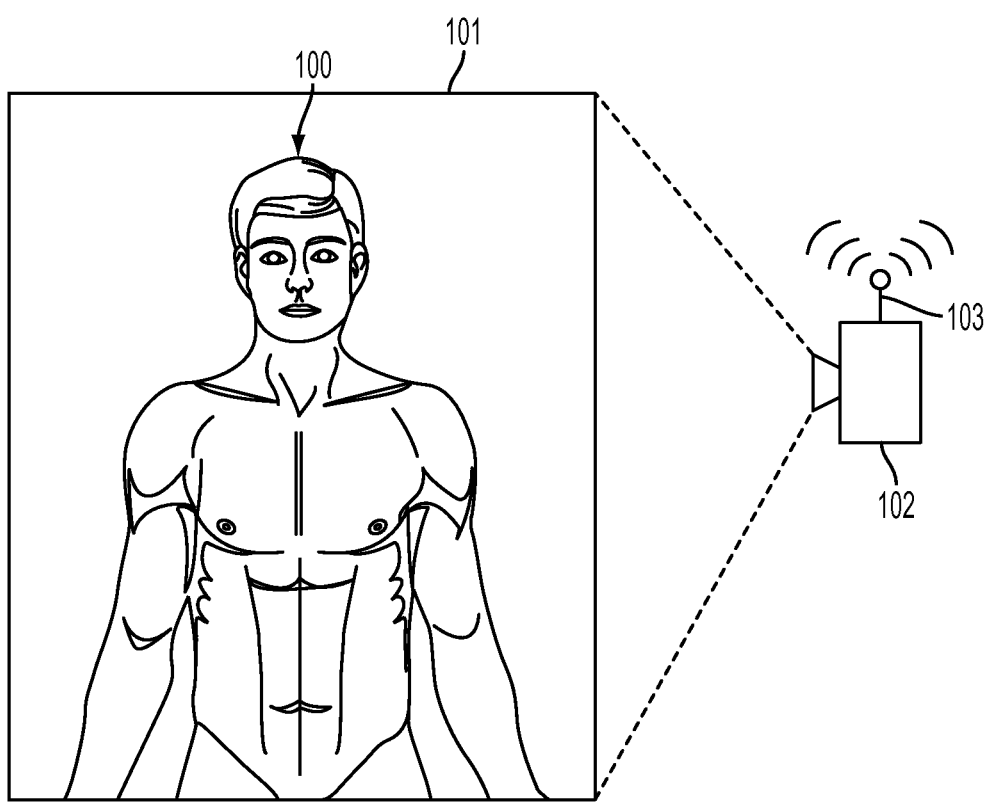
FIG. 1 shows a video image device capturing video of a subject.

A "video imaging device" is a single-channel or a multi-channel video capture device or system capable of registering a videoplethysmographic (VPG) signal on at least one imaging channel. FIG. 1 shows an example video imaging device 102 capturing video 101 of a subject 100. The video is communicated to a remote device via a wireless transmissive element 103, shown as an antenna. The video imaging device may be a device with a high frame rate and high spatial resolution such as, for example, a monochrome camera for capturing black/white video, or a color camera for capturing color video. The video imaging device may be a device with thermal, infrared, multi-spectral or hyperspectral sensors, or may be a hybrid device capable of operating in a conventional video mode with high frame rates and high spatial resolution, and a spectral mode with low frame rates but high spectral resolution. The video imaging device may incorporate various components such as memory, one or more storage devices and processors executing machine readable program instructions for processing and analyzing video in accordance with the teachings hereof. Video imaging devices comprising standard video equipment and those with specialized imaging sensors are readily available from a wide array of vendors in various streams of commerce. The video imaging device may have a plurality of outputs from which the image frames can be retrieved or otherwise received on a per-channel basis.

Figure 2:
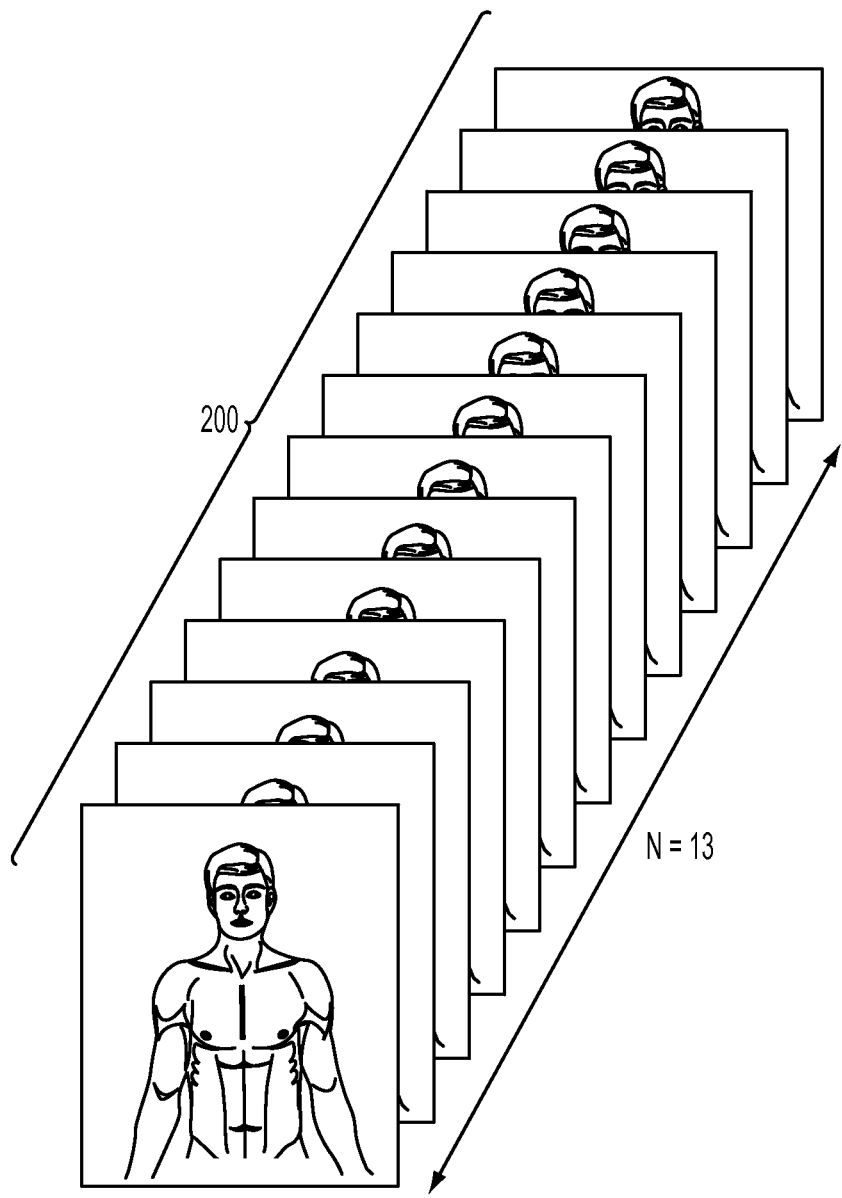
FIG. 2 shows a batch of image frames of the video acquired by the video imaging device of FIG. 1.

"Receiving image frames" of a video is intended to be widely construed and includes: retrieving, capturing, acquiring, or otherwise obtaining image frames for processing. The image frames can be retrieved from a memory or storage device of the video imaging device, obtained from a remote device over a network, or received from a media such as a CDROM or DVD. Image frames may be downloaded from a web-based system or application which makes video available for processing. Image frames can also be received from an application such as those which are available for handheld cellular devices and processed on the cellphone or other handheld computing device such as an iPad or tablet. The image frames of the video are processed in batches. FIG. 2 shows an example batch of 13 temporally successive image frames (collectively at 200) acquired by the video imaging device of FIG. 1. Batches of image frames do not have to be the same size and may vary dynamically during processing. A size N of a batch of image frames is defined such that: $N_{min} \leq N \leq N_{max}$, where $N_{min}$ is a minimum size of a batch of image frames needed to obtain an accurate physiological signal, and $N_{max}$ is a user-defined maximum size of a batch of image frames. For cardiac function assessment, a minimum size of a batch of image frames is preferably not be less than 1 cardiac cycle of the subject. Batches of image frames significantly overlap one another and can be processed using a sliding window when there is a desire to construct the VPG signal on a continuous basis for a longer duration. In one example, a sliding window defines successive batches with 1 second of new image frames and 14 seconds of image frames from a previous batch, (i.e., a 96% overlap). Batches of image frames are processed to isolate regions of exposed skin of the subject in the video.

Figure 3:
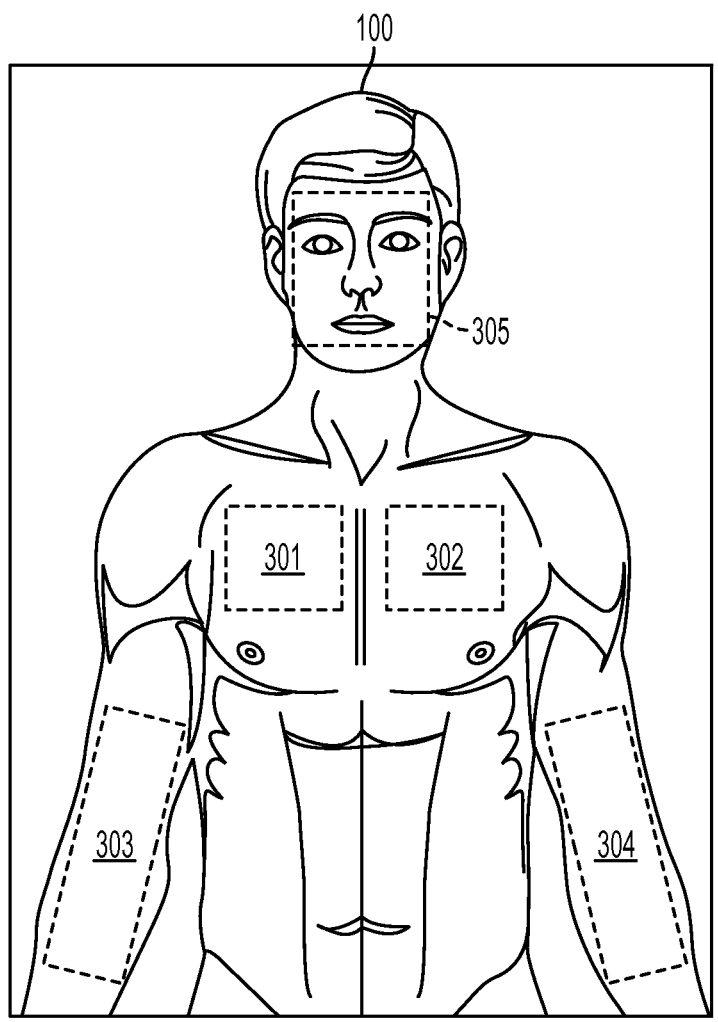
FIG. 3 shows one of the image frames of the batch of FIG. 2 with various regions of exposed skin having been identified for processing.

A "region of exposed skin" refers to an unobstructed view of the subject's skin as seen through the lens of the video imaging device. Regions of exposed skin are isolated in the image frames of the batch where a physiological signal corresponding to the subject's cardiac function was registered by one or more imaging channels of the video imaging device used to capture that video. The region(s) of exposed skin in the image frames are isolated using image processing techniques which include, for instance object identification, pattern recognition, face detection and facial recognition methods, and a pixel classification method as disclosed in the above references by Wang et al. Other methods include color and texture identification, analysis of spatial features, and spectral information. Moreover, a user or technician may use a mouse or a touchscreen display to select or otherwise identify one or more regions of exposed skin in the image frames of the video for processing. Regions of exposed skin in the image frames do not have to be the same size. The regions should at least have a minimum size as defined by the application. The exact size of a given region of exposed skin will vary depending on the application and thus a discussion as to a specific size is omitted. The video imaging device should be zoomed-in to capture a large region of exposed skin to obtain a greater numbers of pixels of skin surface for processing. FIG. 3 shows one of the image frames of the batch of FIG. 2 with a rubber-band box having been drawn around various regions of exposed skin (at 301, 302, 303, 304 and 305). It should be appreciated that the identified regions of FIG. 3 are for explanatory purposes and that other regions of exposed skin may also be identified or otherwise selected, such as the neck or face. FIG. 3 should not be viewed as limiting the scope of the appended claims solely to the illustrated regions of exposed skin. Pixels in the isolated region(s) are processed to obtain a time-series signal. A composite time-series signal may be obtained for all regions or a single time-series signal obtained for each region.

A "time-series signal" is a signal extracted from a batch of image frames that contains frequency components of interest that relate to the cardiac function for which the subject is being monitored. Image frames of the video are processed in batches to isolate one or more regions of exposed skin where the subject's videoplethysmographic (VPG) signal can be registered by one or more imaging channels of the video imaging device. Methods for processing video image frames to identify a time-series signal and for enhancing that signal are disclosed in several of the above references.

In one embodiment, an average of all pixel values in the isolated regions of exposed skin is computed to obtain a channel average on a per-frame basis. A global channel average is computed, for each channel, by adding the channel averages across multiple image frames and dividing by the total number of frames comprising the batch. The channel average is subtracted from the global channel average and the result is divided by a global channel standard deviation to obtain a time-series signal. The time-series signal can be normalized and filtered to remove undesirable frequencies. The time-series signal obtained from processing a given batch of image frames contains the sum total of the relative blood volume changes in the blood vessels close to the skin surface within the isolated region. These arterial pulsations comprise a dominant component of the time-series signals. A videoplethysmographic signal corresponding to the subject's cardiac function is extracted from the time-series signal.

A "videoplethysmographic (VPG) signal" is a physiological signal obtained by performing signal separation on the time-series signal. Methods for extracting a VPG signal from a time-series signal obtained from video images are disclosed in several of the above references.

"Processing" includes the application of any mathematical operation applied to data, according to any specific context, or for any specific purpose as described herein.

A "threshold for movement" is a level of movement during video acquisition to determine whether motion artifacts may have been introduced into the video. If the movement is above the threshold for movement then the current batch of image frames is discarded. Alternatively, an indication is provided that the VPG signal extracted from the time-series signal for this batch may be unreliable and may require further processing. The threshold for movement may be based on a type of motion or a source of motion (i.e., by the subject or by the environment) or the time the movement occurred. The threshold level may be set by a user or technician. The threshold level may be automatically adjusted in real-time or manually adjusted by a user/technician as the video of the subject is being captured by the video imaging device. The threshold for movement will likely depend on the application where the teachings hereof find their intended uses. Therefore, a discussion with respect to a particular threshold level is omitted. Various other responses to movement exceeding the threshold include, for example, initiating an alert signal that movement is excessive; signaling a medical professional that movement has occurred; changing a frame rate of the video imaging device; swapping the video imaging device for another video camera; moving a position of the video imaging device; and stopping video acquisition altogether.

A "fundamental frequency", or simply the "fundamental", is the frequency of a periodic waveform with highest power.

The fundamental is usually abbreviated $f_0$, indicating the frequency as given by:

$$f_0 = \frac{1}{T}$$

where T is the fundamental period. The first harmonic is often abbreviated as $f_1$. In some contexts, the fundamental $f_0$ is the first harmonic. In this context, fundamental frequency is the frequency at which the ventricles contract. For example, during sinus rhythm, fundamental frequency is the largest frequency component present in the signal. The first harmonic is at twice the frequency of the fundamental as described below.

A "harmonic" is a component frequency of a signal that is an integer multiple of the fundamental frequency. If the fundamental frequency is $f_0$, the harmonics have frequencies $2f_0$, $3f_0$, $4f_0$, ..., etc. The harmonics have the property that they are all periodic at the fundamental frequency. Therefore, the sum of harmonics is also periodic at that frequency. Harmonics are equally spaced in frequencies.

A "power spectral density" (PSD), describes how the power of a signal or time series is distributed over the different frequencies contained within that signal. In general, the power P of a signal x(t) is an average over time interval [−T, T], given by:

$$P = \lim_{T \to \infty} \frac{1}{2T} \int_{-T}^{T} x(t)^2 dt$$

It is advantageous to work with a truncated Fourier transform where the signal is integrated only over a finite interval. Methods for computing power spectral density are well understood in the signal processing arts. The reader is directed to the textbooks: "Principles of Random Signal Analysis and Low Noise Design: The Power Spectral Density and its Applications", R. M. Howard (Author), Wiley 1st Ed. (2002), ISBN-13: 978-0471226178, and "Random Signal Analysis in Engineering Systems", John J. Komo (Author), Academic Press (1987), ISBN-13: 978-0124186606.

Figure 4:
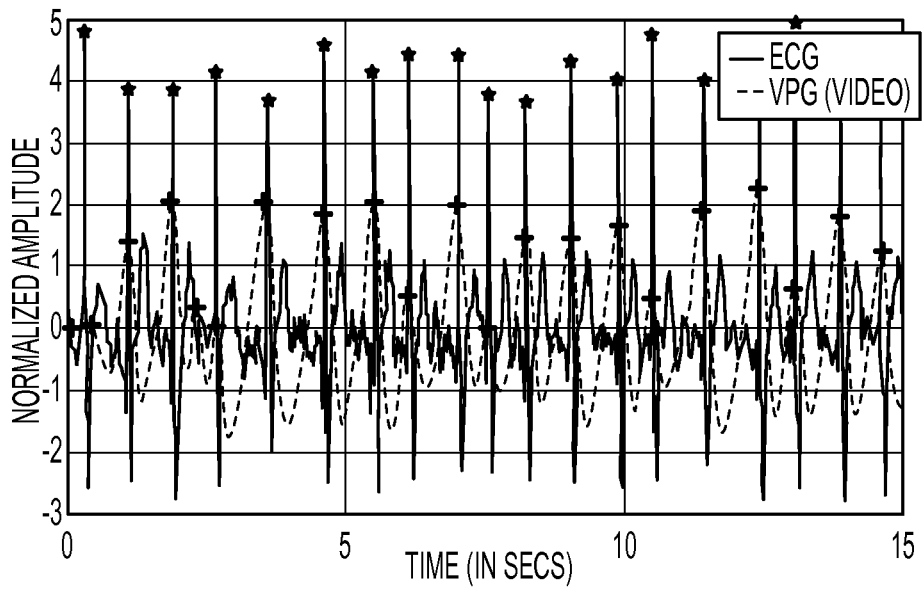
FIG. 4 plots an AF segment with irregular heartbeats.
Figure 5:
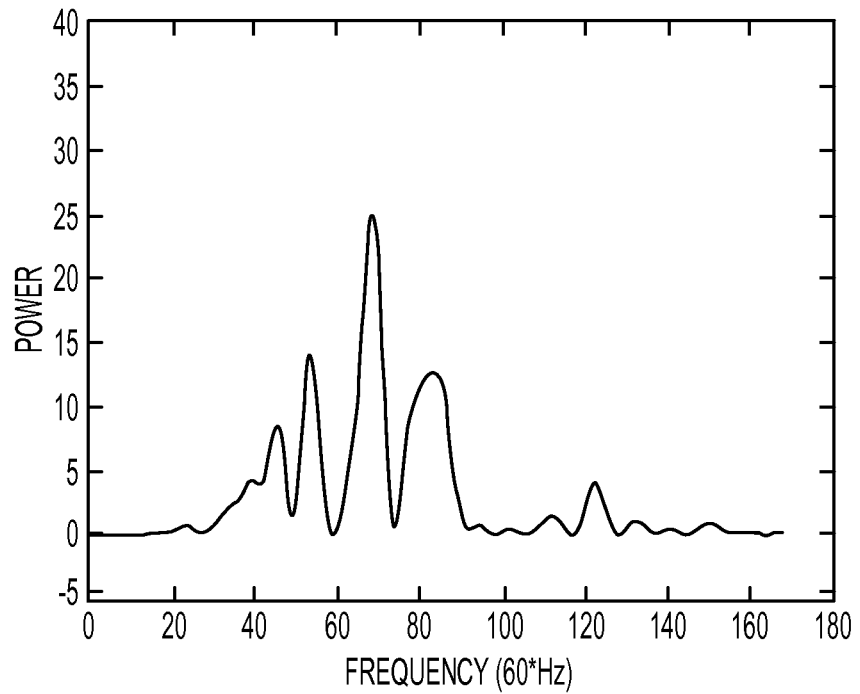
FIG. 5 plots the power distribution of the AF signal segment of FIG. 4.
Figure 6:
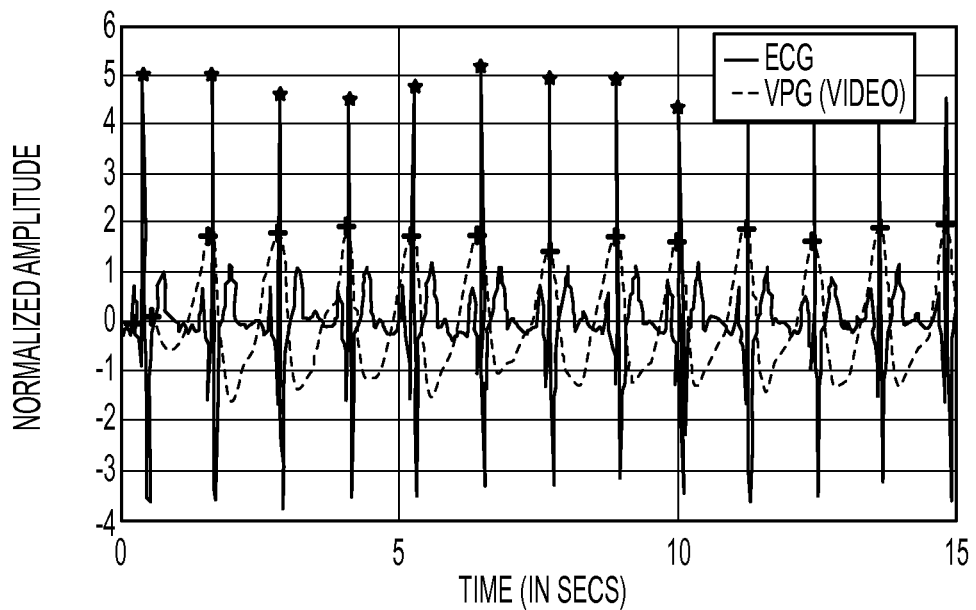
FIG. 6 plots the sinus rhythm (SR) when the beat-to-beat interval is consistent.
Figure 7:
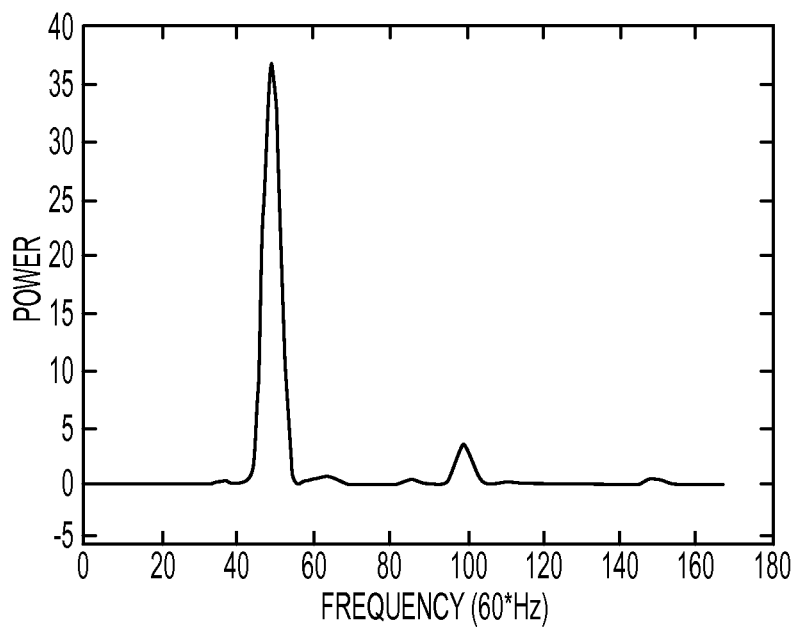
FIG. 7 plots the power distribution of the SR signal segment of FIG. 6.

Due to irregularity in heart beats during AF (FIG. 4), the power is distributed along different frequencies (as shown in FIG. 5). As a result power of the fundamental frequency is low when compared to the same during sinus rhythm. While in sinus rhythm when the beat-to-beat interval is mostly consistent (FIG. 6), the power is more concentrated around the pulse frequency (as shown in FIG. 7). In FIG. 7, the first few harmonics of the pulse frequency can be observed. These features are used to compute pulse harmonic strength. In FIGS. 4 and 6, the ECG signal overlaps the VPG signals and the VPG signals were shifted to compensate for a delay associated with pulse transmit time.

"Pulse harmonic strength (PHS)" is a ratio of signal strength at the fundamental frequency and harmonics to a strength of a base signal without these fundamental frequency and harmonics. From the PSD, the fundamental frequency and its harmonics are identified. Frequencies in a neighborhood of the harmonics can also be considered by defining a band (e.g., 0.2 Hz or 12 beats per minutes (bpm)). All the power is integrated within this band, denoted $P_{sig}$. Power in all remaining bands are integrated separately, denoted $P_{noi}$. The pulse harmonic strength is therefore given by the ratio:

$PHS = P_{sig}/P_{noi}$ $P_{noi} = P_{Total} - P_{sig}$.

where $P_{Total}$ is the total energy of the signal.

The PHS therefore represents the total strength of the pulse power because the power is centered at heart beats and the harmonics of those beats.

"Normalized pulse harmonic strength (NPHS)" is a ratio of signal strength at the fundamental frequency and harmonics to a strength of a base signal. The normalized pulse harmonic strength is therefore given by the ratio:

$NPHS = P_{sig}/P_{Total}$

The normalized PHS has a value between 0 and 1.

Figure 8:
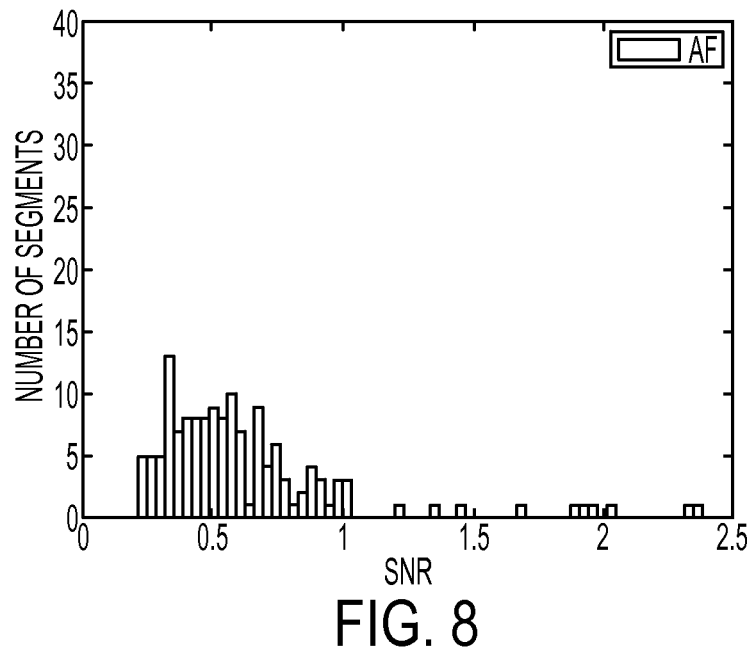
FIG. 8 is a histogram of the pulse power or PHS of various AF segments collected across different patients for a total of 11 AF patients.
Figure 9:
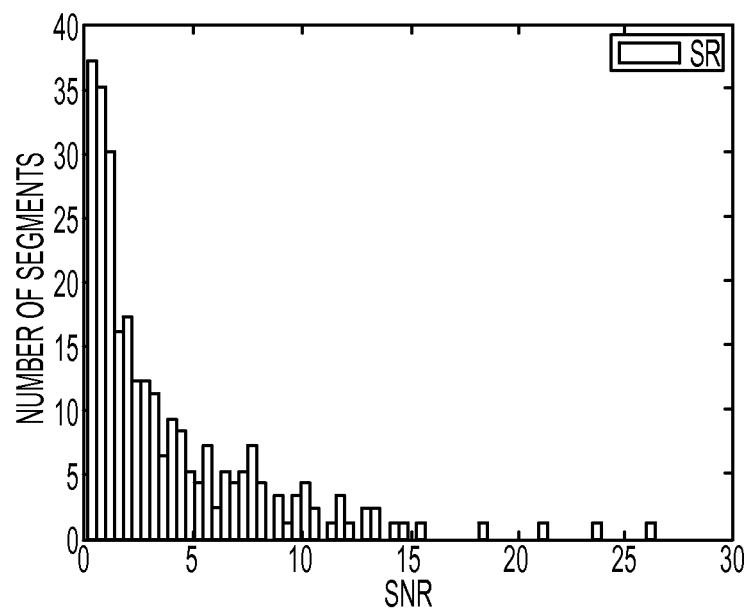
FIG. 9 is a histogram of the pulse power or PHS of various SR segments for the same patient pool recovered after cardioversion.

FIG. 8 is a histogram of the pulse power of the AF segment of FIG. 5. FIG. 9 is a histogram of the pulse power of the SR segment of FIG. 7. In an ideal scenario, PHS would be low for AF and high for SR. The present method utilizes a discrimination threshold to classify AF from SR. The threshold is based on a distribution of PHS values over a large dataset.

A "Receiver Operating Characteristic (ROC) curve" is a graphical plot which illustrates the performance of a binary classifier system as its discrimination threshold is varied. The ROC is created by plotting the fraction of true positives out of the total actual positives (TPR=true positive rate) vs. the fraction of false positives out of the total actual negatives (FPR=false positive rate), at various discrimination threshold levels. TPR is also known as sensitivity. The FPR is also known as the fall-out and can be calculated as one minus the well-known specificity. The ROC curve is then the sensitivity as a function of fall-out. In general, if both of the probability distributions for detection and false alarm are known, the ROC curve plots the Cumulative Distribution Function (area under the probability distribution from −∞ to +∞) of the detection probability along the y-axis versus the Cumulative Distribution Function of the false alarm probability along the x-axis. ROC analysis tools select possibly optimal models and discard suboptimal ones independently from the cost context or the class distribution. ROC analysis has been used in medicine, radiology, biometrics, and other areas for many decades and is increasingly used in machine learning and data mining. For a more in-depth recitation, the reader is directed to the textbook: "*Analyzing Receiver Operating Characteristic Curves With SAS*", Mithat Gonen, SAS Institute; 1st Edition (2007), ISBN-13: 978-1599942988, and to the paper: "*ROC Graphs: Notes and Practical Considerations for Researchers*", Tom Fawcett, Kluwer Academic Publishers, Netherlands, (2004).

Figure 10:
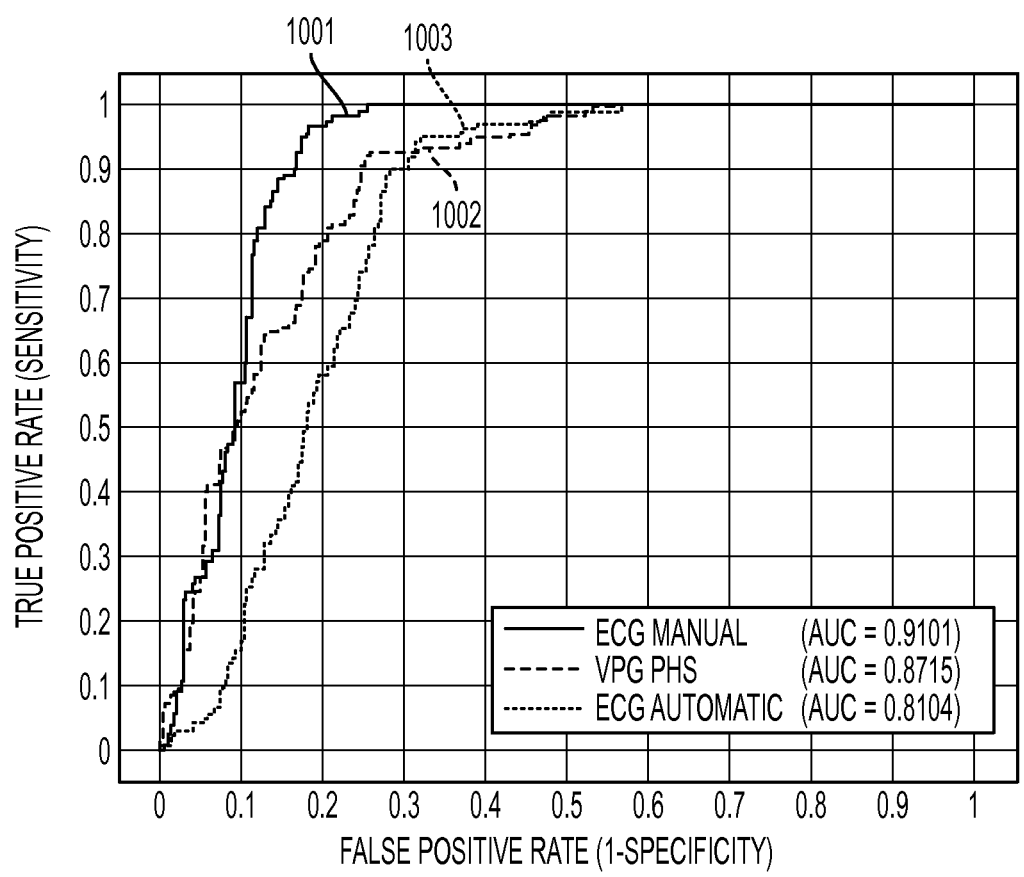
FIG. 10 shows a ROC curve.

The "discrimination threshold" is used herein to determine whether the subject in the video is having an AF episode or is in sinus rhythm (SR). A Receiver Operating Characteristic (ROC) curve facilitates a determination of the discrimination threshold which separates low PHS values from high PHS values. It should be appreciated that, as the threshold is varied, the sensitivity and specificity vary. In FIG. 10, the curve 1001 is the ROC curve for ECG Manual. Well-known SDRR metrics were used for manually annotated ECG data. Curve 1003 is the ROC curve for ECG Automatic. SDRR metrics were also utilized for this data as well. A filtering algorithm was used to remove incorrect or ectopic beats from the VPG signal data, i.e., beats greater than or less than 20% of adjacent beats. The filtering method is disclosed in: "*Filtering Poincare Plots*", J. Piskorski, P. Guzik, Computational Methods in Science and Technology, 11(1), pp. 39-48, (2005). Curve 1002 is the ROC curve obtained from the VPG signal data. Here, our present PHS metric was used for this curve. In the ROC curve for PHS, when the specificity is 100% and the sensitivity is 100%, (i.e., point (1,0) in FIG. 10), the measurement is considered to be nearly perfect. At about 50% specificity, all three curves show 100% sensitivity. For about 80% specificity, the VPG data shows 80% sensitivity, i.e., the VPG method gives 80% of the time actual positive values with correct identification. For 80% specificity, the present method is very powerful when compared to ECG Automatic based on the SDRR metrics, since the sensitivity for ECG Automatic is about 60%.

A "remote sensing environment" refers to the non-contact, unobtrusive, non-invasive acquisition of video images of a subject. The video imaging device can be any distance away from the subject, for example, as close as less than an inch to as far as miles in the case of telemedicine. The teachings hereof advantageously find their uses in a remote sensing environment such that the resting patient is undisturbed.

Flow Diagram of One Example Embodiment

Figure 11:
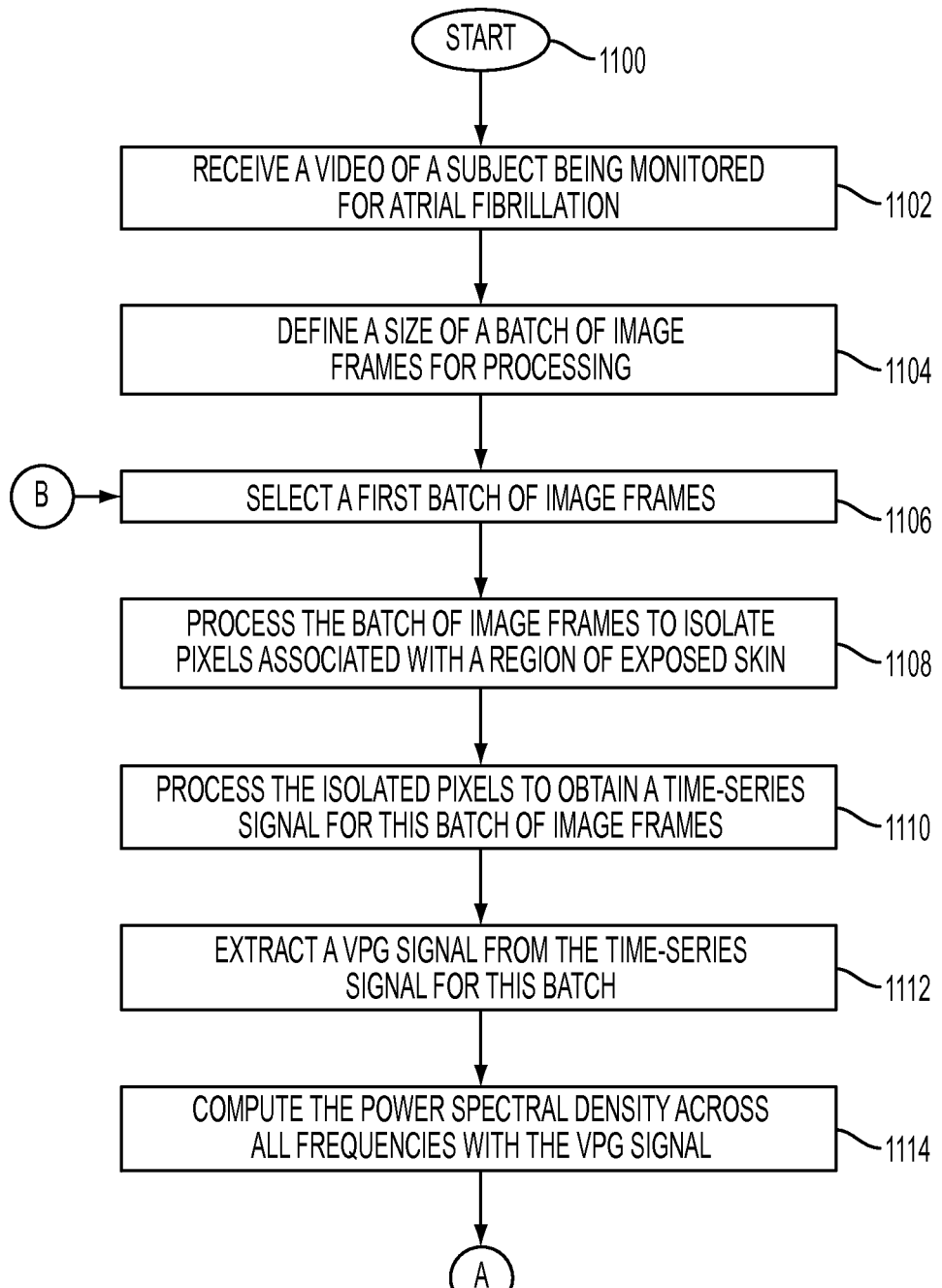
FIG. 11 is a flow diagram which illustrates one example embodiment of the present method for determining whether a subject is having an atrial fibrillation event.

Reference is now being made to the flow diagram of FIG. 11 which illustrates one example embodiment of the present method for determining whether a subject is having an atrial fibrillation event. Flow processing begins at step 1100 and immediately proceeds to step 1102.

At step 1102, receive a video of a subject being monitored for atrial fibrillation. The video is of a region of exposed skin of a subject where a videoplethysmographic (VPG) signal can be registered by at least one imaging channel of a video imaging device used to capture that video.

At step 1104, define a size N of a batch of image frames for processing. The size is such that $N_{min} \leq N \leq N_{max}$, where $N_{min}$ is a minimum size of a batch of image frames and $N_{max}$ is a maximum size of a batch of image frames.

At step 1106, select a first batch of image frames of size N.

At step 1108, process the batch of image frames (of step 1106) to isolate pixels associated with the region of exposed skin.

At step 1110, process the isolated pixels to obtain a time-series signal for this batch of image frames.

At step 1112, extract a VPG signal from the time-series signal for this batch.

At step 1114, compute a power spectral density across all frequencies within the VPG signal.

Figure 12:
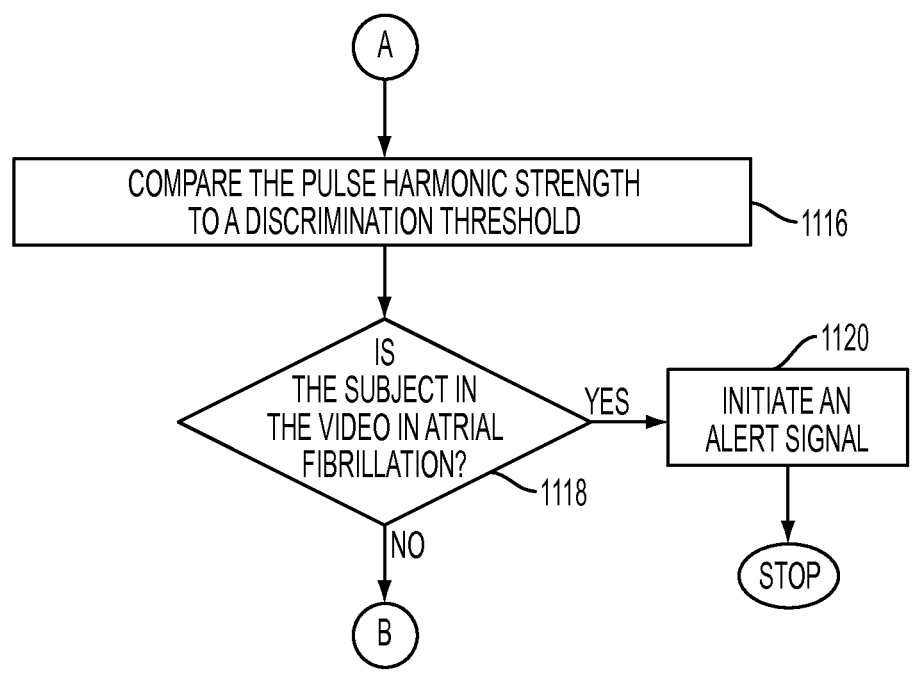
FIG. 12 which is a continuation of the flow diagram of FIG. 11 with flow processing continuing with respect to node A.

Reference is now being made to the flow diagram of FIG. 12 which is a continuation of the flow diagram of FIG. 11 with flow processing continuing with respect to node A.

At step 1116, compare the pulse harmonic strength to a pre-determined discrimination threshold which may be obtained using a Receiver Operating Characteristic (ROC) curve or patient VPG signals during AF and sinus.

At step 1118, a determination is made whether, as a result of the comparison, that the subject is in atrial fibrillation. If the subject is in atrial fibrillation then, at step 1120, an alert signal is provided. The alert may take the form of a message displayed on a display device or a sound activated at, for example, a nurse's station or a display of a device. The alert may take the form of a colored or blinking light which provides a visible indication that an alert condition exists. The alert can be a text, audio, and/or video message. The alert signal may be communicated to one or more remote devices over a wired or wireless network. The alert may be sent directly to a handheld wireless cellular device of a medical professional. Thereafter, additional actions would be taken in response to the alert. In this embodiment, after the alert signal is initiated, further processing stops. In other embodiments, flow processing continues in a similar manner. If, at step 1118, it is determined that the subject not in atrial fibrillation, i.e., is in normal sinus rhythm then, in this embodiment, processing continues with respect to node B wherein, at step 1106, a next batch is selected or is otherwise identified for processing. It is to be noted that the next batch may be selected immediately following the current batch or with overlap as described above depending on the duration over which monitoring is required. Processing continues in a similar manner for the next batch. The method hereof is preferably used for patient monitoring where the image frames of the video are captured by the video imaging device in real-time and processed as they are received on a continuous basis or until video acquisition is terminated.

It should also be appreciated that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Video Processing System

Figure 13:
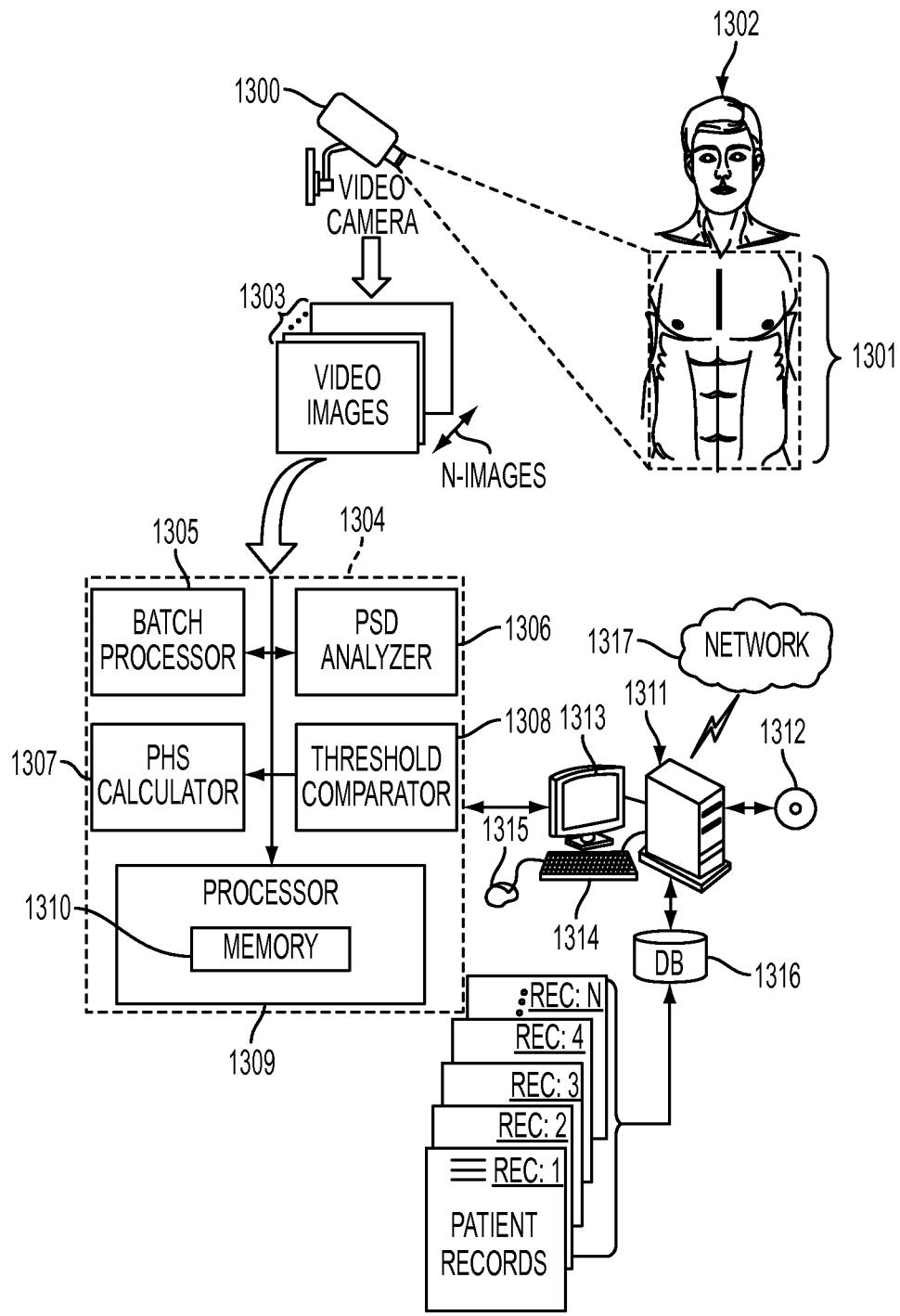
FIG. 13 is a block diagram of one example video processing system for processing a video in accordance with the embodiment described with respect to the flow diagrams of FIGS. 11 and 12.

Reference is now being made to FIG. 13 which shows a block diagram of one example video processing system 1300 for processing a video in accordance with the embodiment described with respect to the flow diagrams of FIGS. 11 and 12.

In FIG. 13, video imaging device 1300 is shown acquiring streaming video of an exposed body region 1301 of the subject 1302. Video image frames (collectively at 1303) are communicated to the video processing system 1304 wherein various aspects of the methods disclosed herein are performed.

Batch processor 1305 receives the defined size N of a batch of image frames from the workstation 1311 and continuously processes batches of image frames of size N by isolating pixels associated with the exposed body region in the image frames and then processing the isolated pixels to obtain a time-series signal for each batch. The batch processor further extracts a VPG signal from the time-series signal. PSD Analyzer 1306 receives the VPG signal and computes a power spectral density across all frequencies within the VPG signal. PHS Calculator 1307 calculates a pulse harmonic strength for the VPG signal. Threshold Comparator 1308 compares the pulse harmonic strength to a discrimination threshold which is retrieved from the workstation 1311. As a result of this comparison, a determination is made whether the subject in the video is in atrial fibrillation or in sinus rhythm.

Central Processor (CPU) 1309 retrieves machine readable program instructions from Memory 1310 and is provided to facilitate the functionality of any of the modules of the video processing system 1304. The processor 1309, operating alone or in conjunction with other processors and memory, may be configured to assist or otherwise perform the functionality of any of the processors and modules of system 1304. Processor 1309 proceeds to generate a physiological signal from the various time-series signals and communicates the subject's physiological signal to the display device of workstation 1311.

A computer case of the workstation 1311 houses various components such as a motherboard with a processor and memory, a network card, a video card, a hard drive capable of reading/writing to machine readable media 1312 such as a floppy disk, optical disk, CD-ROM, DVD, magnetic tape, and the like, and other software and hardware needed to perform the functionality of a computer workstation. The workstation further includes a display device 1313, such as a CRT, LCD, or touchscreen device, for displaying information, video, measurement data, computed values, medical information, results, locations, and the like. A user can view any of that information and make a selection from menu options displayed thereon. Keyboard 1314 and mouse 1315 effectuate a user input or selection.

The workstation implements a database in storage device 1316 wherein patient records are stored, manipulated, and retrieved in response to a query. Such records, in various embodiments, take the form of patient medical history stored in association with information identifying the patient along with medical information. Although the database is shown as an external device, the database may be internal to the workstation mounted, for example, on a hard disk therein. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing image frames. The workstation is further enabled to display the image frames comprising the video.

In other embodiments, a user or technician may use the user interface of the workstation to identify areas of interest, set parameters, select image frames and/or regions of images for processing. These selections may be stored/retrieved in a storage devices 1312 and 1316. Default settings and initial parameters can be retrieved from any of the storage devices shown, as desired. Further, a user may adjust the various parameters being employed or dynamically settings in real-time as successive batches of image frames are received for processing.

Although shown as a desktop computer, it should be appreciated that the workstation can be a laptop, mainframe, or a special purpose computer such as an ASIC, circuit, or the like. The embodiment of the workstation of FIG. 13 is illustrative and may include other functionality known in the arts. Any of the components of the workstation may be placed in communication with the video processing system 1304 or any devices in communication therewith. Moreover, any of the modules and processing units of system 1304 can be placed in communication with storage device 1316 and/or computer media 1312 and may store/retrieve therefrom data, variables, records, parameters, functions, and/or machine readable/executable program instructions, as needed to perform their intended functions.

Each of the modules of the video processing system may be placed in communication with one or more remote devices over network 1317. It should be appreciated that some or all of the functionality performed by any of the modules or processing units of system 1304 can be performed, in whole or in part, by the workstation placed in communication with the video imaging device 1300 over network 1317. The embodiment shown is illustrative and should not be viewed as limiting the scope of the appended claims strictly to that configuration. Various modules may designate one or more components which may, in turn, comprise software and/or hardware designed to perform the intended function.

Performance Results

Initially, a face region of interest (ROI) was manually selected from a first image frame of a batch of image frames of a video of the subject. Motion tracking of the ROI was utilized to automatically select multiple video segments of 15 seconds when no movement occurred or when the movement was determined to be below a threshold level pre-defined for movement. The image frames from the batches were processed and a VPG signal extracted from each batch. Thereafter, PSD was computed and the PHS was determined from the PSD. A total of 407 video segments were processed. ECG RR intervals and manual annotations for the corresponding video segments were found at the same time. For AF, PHS values were found to lie in a much lower range when compared to the range of PHS values for SR. The data structure was that of both clustered and correlated data, given that we obtained a random number of repeated measurements (one per 15-second epoch) on multiple candidate predictors of AF from each of 11 patients in both AF and SR periods. The ability of each candidate predictor to classify each of the 407 epochs (i.e., segments or batches) was assessed as either AF (n=143) or SR (n=264).

Leave-one-subject-out cross-validation was used to estimate the classification error rate (CER) of each method. This was done by selecting the threshold that optimized the epoch-level CER for 10 training subjects; computing the empirical CER for the epochs from the 1 test subject, using the training threshold; and computing the weighted average of the 11 subject-specific cross-validated error rates, weighted by the number of epochs per subject. Sensitivity of VPG-based PHS was compared with that of each ECG-based parameters, for each level of specificity, using nonparametric analysis of clustered ROC curve data. Separate linear mixed effect models for AF and for SR, each with a random effect for subject, were used to model each continuous predictor (VPG, and the ECG-based measures), thus providing period-specific means and standard errors (SE). Linear mixed effect models with a fixed effect for AF (versus SR) and a random effect for subject facilitated an estimation of the difference in period-specific means, along with the SE and p-value for the difference. All hypothesis tests were 2-sided 0.05 level tests.

Figure 14:
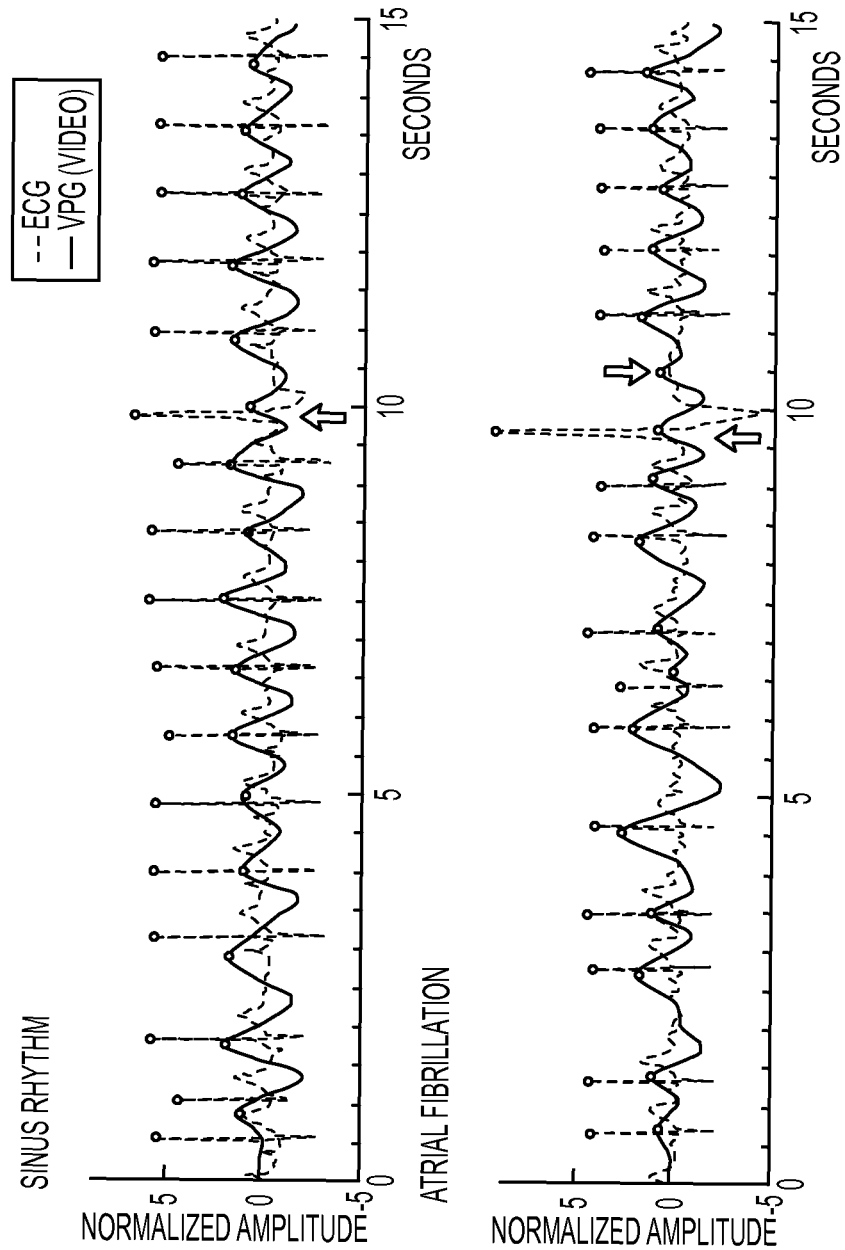
FIG. 14 shows examples of synchronized 15-sec ECG and VPG signals after successful cardioversion (upper panel) and during atrial fibrillation (lower panel)

The two panels of FIG. 14 present the superimposed plots of the VPG and the ECG signals to illustrate the VPG signal patterns, the synchronization between pulsatile and RR intervals, and cases of ventricular premature contractions. The VPG signals was shifted to compensate for the delay associated with the pulse transmit time. Circles mark the R waves and pulse peaks of the ECG and VPG signals, respectively. The VPG and ECG signals were normalized to zero mean and unit variance in both panels. The arrow in the upper panel describes a case of VPC detected on the VPG signal. In the lower panel, the first arrow shows VPCs detection and the second a case of over detection of pulse rate. In order to facilitate a comparison of time occurrence of the QRS complexes and the peak of the VPG signals, we synchronized the signal after elimination of delay due to the pulse transit time (artificially synchronizing first QRS complex with first pulse peak).

The Table of FIG. 15 shows average values and standard errors for the parameters measuring the dispersion of the heart and the pulsatile rates. All investigated factors computed from the ECG signals and the VPG signals show a significant increased variability during AF in comparison to sinus rhythm ($p<0.0001$). However, the difference between the two periods for SDRR, RMSSD, pNN50, SD1, and SD2 are larger when based on ECG signal.

Figure 16:
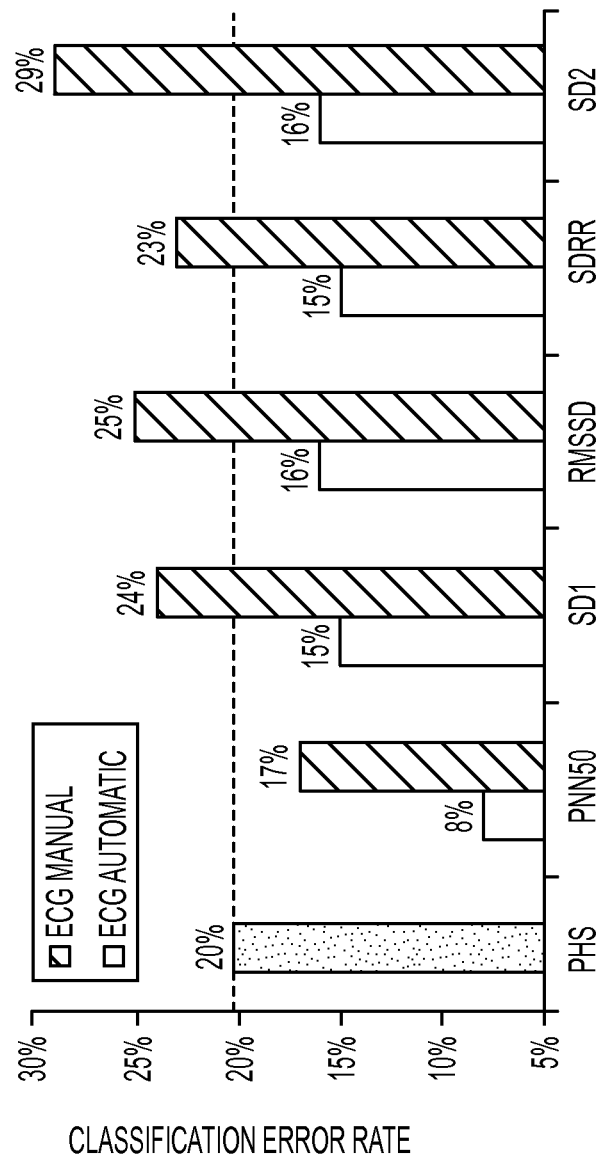
FIG. 16 shows the estimated error rate in classifying 15-sec epochs based on PHS and other ECG-based time-domain quantifiers of heart rate variability for 11 AF patients.

FIG. 16 shows the estimated error rate in classifying 15-sec epochs based on PHS and other ECG-based quantifiers of heart rate variability. Leave-one-subject-out cross-validation was used to avoid the optimism otherwise associated with adaptively selecting the optimal classification threshold. Linear mixed effects models were used to estimate the mean (standard error) of the investigated factors for AF and SR periods, as well as the difference ($\Delta$), along with the p-value for the difference.

Figure 17A:
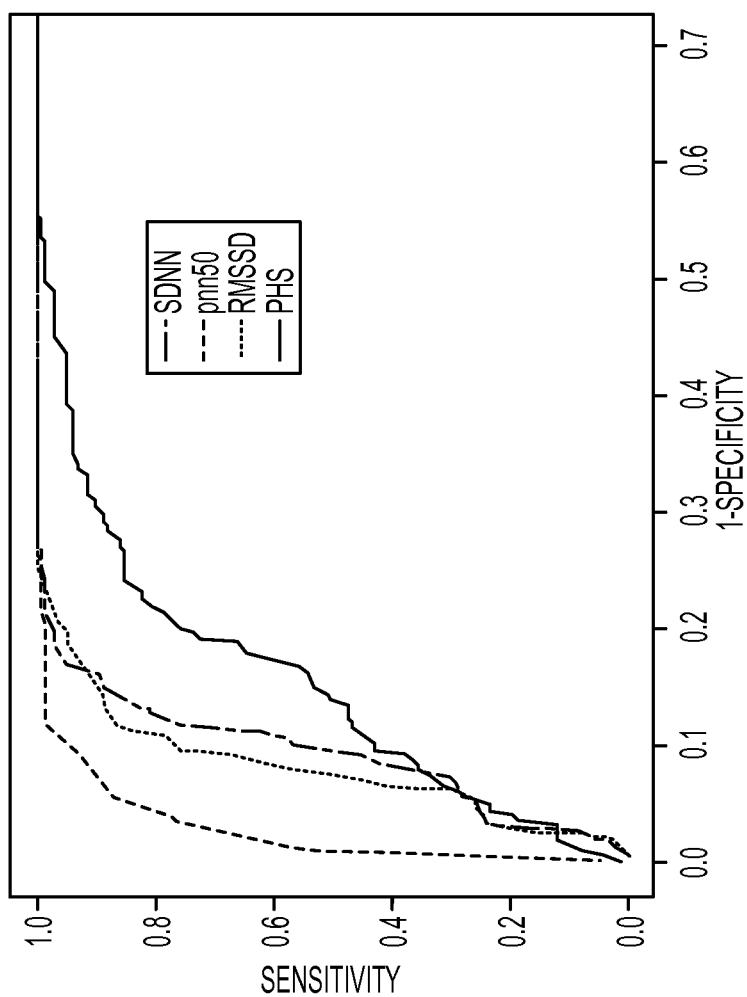
FIGS. 17A-B show ROC curves for comparing VPG-based PHS and for ECG-based parameters quantifying the variability of heart and pulse rates.
Figure 17B:
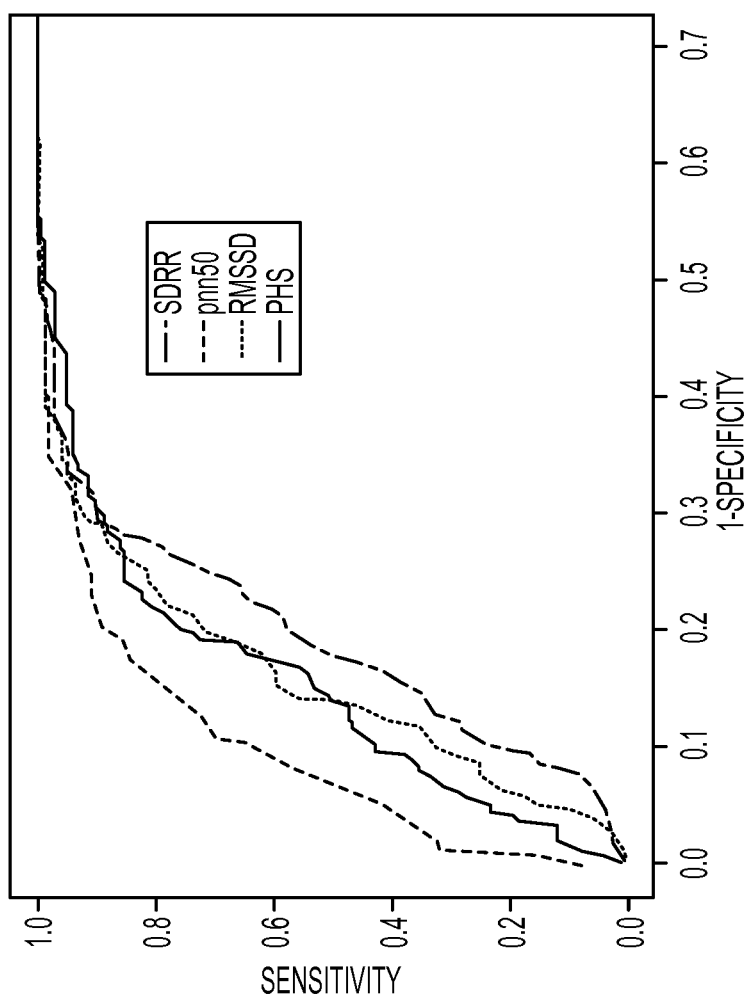

FIGS. 17A-B show ROC curves for comparing VPG-based PHS and for ECG-based parameters quantifying the variability of heart and pulse rates. In FIG. 17A, automated VPG is compared with adjudicated ECG measures. In FIG. 17B, automated VPG is compared with automated ECG measures.

Based on these results, the methods disclosed herein have a potential to shift the paradigm of AF detection.

Various Embodiments

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture which may be shipped, sold, leased, or otherwise provided separately either alone or as part of a product suite or a service.

It will be appreciated that the above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any textbooks, papers, or other publications referenced herein are each hereby incorporated herein in their entirety by reference.

What is claimed is:

1. A method for determining whether a subject is having an atrial fibrillation event, the method comprising:
   receiving a video of a region of exposed skin of a subject where a videoplethysmographic (VPG) signal can be registered by at least one imaging channel of a video imaging device used to capture that video;
   defining a size N of a batch of image frames such that $N_{min} \leq N \leq N_{max}$, where $N_{min}$ is a minimum size of a batch of image frames and $N_{max}$ is a maximum size of a batch of image frames; and
   for each batch of image frames of size N:
      processing this batch of image frames to isolate pixels associated with said region of exposed skin;
      processing said isolated pixels to obtain a time-series signal for this batch;
      extracting a VPG signal from said time-series signal;
      computing a power spectral density across all frequencies within said VPG signal;
      calculating a pulse harmonic strength for this VPG signal;
      comparing the pulse harmonic strength (PHS) to a discrimination threshold obtained from a Receiver Operating Characteristic (ROC) curve constructed from health vitals obtained for a group of cardiac patients, said threshold discriminating between low PHS values and high PHS values; and
      classifying, as a result of said comparison, that said subject is one of: in atrial fibrillation, and in sinus rhythm, wherein when PHS is below said threshold said subject is classified as being in atrial fibrillation, and in normal sinus rhythm otherwise.

2. The method of claim 1, wherein said video image frames comprise any combination of: Near Infrared (NIR) images, color images, color with NIR images, multispectral images, and hyperspectral video images.

3. The method of claim 1, wherein said pulse harmonic strength for said VPG signal is a normalized pulse harmonic strength.

4. The method of claim 1, wherein, in advance of obtaining said time-series signal, pre-processing said video to compensate for any of: an imaging blur, and slow illuminant variation.

5. The method in claim 1, wherein said time-series signal is detrended to remove non-stationary signal components.

6. The method of claim 1, further comprising filtering said time-series signal with a bandpass filter with a low and high cutoff frequency defined as a function of said subject's cardiac pulse frequency.

7. The method of claim 6, further comprising filtering said VPG signal to remove unwanted artifacts, said filtering using at least one of: a Fast Fourier Transform (FFT)-based phase preservation filter, a zero-phase digital filter, a linear time invariant filter, a linear time varying filter, a finite impulse response filter, an infinite impulse response filter, a non-linear filter and a moving average filter.

8. The method in claim 1, wherein, said power spectral density is computed by performing any of: a non-parametric and a parametric spectral density estimation on the time-series signal.

9. The method of claim 1, wherein said discrimination threshold is based on a obtained VPG signal from the subject during one of: atrial fibrillation, sinus rhythm.

10. The method of claim 1, further comprising determining whether a movement occurred during video acquisition of a batch of image frames and, in response to said movement being above a predetermined threshold level for movement, not processing the current batch of image frames.

11. The method of claim 1, further comprising upsampling said time-series signal to a standard sampling frequency.

12. The method of claim 1, wherein, in response to said subject having an atrial fibrillation event, further comprising any of: initiating an alert and signaling a medical professional.

13. The method of claim 1, further comprising dynamically adjusting a size of said batch of image frames.

14. The method of claim 1, wherein said video is a streaming video and said determination of an atrial fibrillation event occurs in real-time.

15. A system for determining whether a subject is having an atrial fibrillation event, the system comprising:
   a memory and a storage device; and
   a processor in communication with said memory and storage device, said processor executing machine readable instructions for performing:
      receiving a video of a region of exposed skin of a subject where a videoplethysmographic (VPG) signal can be registered by at least one imaging channel of a video imaging device used to capture that video;
      defining a size N of a batch of image frames such that $N_{min} \leq N \leq N_{max}$, where $N_{min}$ is a minimum size of a batch of image frames and $N_{max}$ is a maximum size of a batch of image frames; and
      for each batch of image frames of size N:
         processing this batch of image frames to isolate pixels associated with said region of exposed skin;
         processing said isolated pixels to obtain a time-series signal for this batch;
         extracting a VPG signal from said time-series signal;
         computing a power spectral density across all frequencies within said VPG signal;
         calculating a pulse harmonic strength for this VPG signal;
         comparing the pulse harmonic strength (PHS) to a discrimination threshold obtained from a Receiver Operating Characteristic (ROC) curve constructed from health vitals obtained for a group of cardiac patients, said threshold discriminating between low PHS values and high PHS values; and
         classifying, as a result of said comparison, that said subject is one of: in atrial fibrillation, and in sinus rhythm, wherein when PHS is below said threshold said subject is classified as being in atrial fibrillation, and in normal sinus rhythm otherwise.

16. The system of claim 15, wherein said video image frames comprise any combination of: Near Infrared (NIR)

images, color images, color with NIR images, multispectral images, and hyperspectral video images.

17. The system of claim 15, wherein said pulse harmonic strength for said VPG signal is a normalized pulse harmonic strength.

18. The system of claim 15, wherein, in advance of obtaining said time-series signal, pre-processing said video to compensate for any of: an imaging blur, and slow illuminant variation.

19. The system of claim 15, wherein, said time-series signal is detrended to remove non-stationary signal components.

20. The system of claim 15, further comprising filtering said time-series signal with a bandpass filter with a low and high cutoff frequency defined as a function of said subject's cardiac pulse frequency.

21. The system of claim 20, further comprising filtering said VPG signal to remove unwanted artifacts, said filtering using at least one of: a Fast Fourier Transform (FFT)-based phase preservation filter, a zero-phase digital filter, a linear time invariant filter, a linear time varying filter, a finite impulse response filter, an infinite impulse response filter, a non-linear filter and a moving average filter.

22. The system of claim 15, wherein, said power spectral density is computed by performing any of: a non-parametric and a parametric spectral density estimation on the time-series signal.

23. The system of claim 15, wherein said discrimination threshold is based on a obtained VPG signal from the subject during one of: atrial fibrillation, sinus rhythm.

24. The system of claim 15, further comprising determining whether a movement occurred during video acquisition of a batch of image frames and, in response to said movement being above a predetermined threshold level for movement, not processing the current batch of image frames.

25. The system of claim 15, further comprising upsampling said time-series signal to a standard sampling frequency.

26. The system of claim 15, wherein, in response to said subject having an atrial fibrillation event, further comprising any of: initiating an alert and signaling a medical professional.

27. The system of claim 15, further comprising dynamically adjusting a size of said batch of image frames.

28. The system of claim 15, wherein said video is a streaming video and said determination of an atrial fibrillation event occurs in real-time.

\* \* \* \* \*